(12) United States Patent
Oka et al.

(10) Patent No.: US 8,945,195 B2
(45) Date of Patent: Feb. 3, 2015

(54) SMALL BOWEL ENDOSCOPE OF ILEUS TUBE TYPE THAT ENABLES LASER INSPECTION AND THERAPY

(75) Inventors: Kiyoshi Oka, Naka-gun (JP); Tomoaki Toriya, Sakura (JP); Takashi Tsumanuma, Sakura (JP); Kenichi Nakatate, Sakura (JP); Junji Yoshino, Toyoake (JP); Takao Wakabayashi, Toyoake (JP)

(73) Assignees: Japan Atomic Energy Agency, Ibaraki (JP); Fujikura Ltd., Tokyo (JP)

( * ) Notice: Subject to any disclaimer, the term of this patent is extended or adjusted under 35 U.S.C. 154(b) by 2330 days.

(21) Appl. No.: 11/356,123

(22) Filed: Feb. 17, 2006

(65) Prior Publication Data
US 2006/0190006 A1 Aug. 24, 2006

(30) Foreign Application Priority Data
Feb. 21, 2005 (JP) .................................. 2005-43598

(51) Int. Cl.
| | | |
|---|---|---|
| A61N 5/067 | (2006.01) |
| A61B 18/24 | (2006.01) |
| A61B 1/00 | (2006.01) |
| A61B 5/00 | (2006.01) |
| A61B 1/04 | (2006.01) |
| A61B 1/233 | (2006.01) |
| A61B 19/00 | (2006.01) |

(52) U.S. Cl.
CPC .............. *A61B 18/24* (2013.01); *A61B 5/0084* (2013.01); *A61B 1/00165* (2013.01); *A61B 1/00167* (2013.01); *A61B 1/042* (2013.01); *A61B 1/233* (2013.01); *A61B 2019/5206* (2013.01); *A61B 2019/5217* (2013.01)

USPC .......................................................... 607/88

(58) Field of Classification Search
USPC ................. 606/2–51; 600/104, 182; 385/116; 607/88–95
See application file for complete search history.

(56) References Cited

U.S. PATENT DOCUMENTS

| | | | | |
|---|---|---|---|---|
| 4,875,897 A | * | 10/1989 | Lee .............................. 604/536 |
| 4,896,941 A | * | 1/1990 | Hayashi et al. ............... 385/116 |
| 5,293,872 A | * | 3/1994 | Alfano et al. ................. 600/475 |
| 6,091,872 A | * | 7/2000 | Katoot .......................... 385/116 |
| 6,129,662 A | * | 10/2000 | Li et al. ........................ 600/182 |

(Continued)

FOREIGN PATENT DOCUMENTS

| | | |
|---|---|---|
| JP | 60-181703 | 12/1985 |
| JP | 60-181704 | 12/1985 |

(Continued)

OTHER PUBLICATIONS

Japanese Office Action for corresponding Japanese Application 2005-043598; dated Feb. 22, 2010.
Japanese Office Action issued Nov. 11, 2010 in corresponding Japanese Patent Application 2005-043598.

(Continued)

*Primary Examiner* — Aaron Roane
(74) *Attorney, Agent, or Firm* — Staas & Halsey LLP

(57) ABSTRACT

A small bowel endoscopic system of an ileus tube type using a monolithic composite optical fiber that can be applied with an ileus tube employed to administer a contrast agent or the like to a patient suffering from ileus and which is an integral assembly of a large-diameter optical fiber with a core/cladding structure intended for laser light transmission and a multi-core image fiber section surrounding that optical fiber to enable image transmission.

14 Claims, 3 Drawing Sheets

Small bowel endoscope used with an ileus tube (in longitudinal section)

(56) References Cited

U.S. PATENT DOCUMENTS

| | | | |
|---|---|---|---|
| 6,597,941 B2 * | 7/2003 | Fontenot et al. | 600/473 |
| 6,761,713 B2 * | 7/2004 | Teichmann | 606/10 |
| 6,845,193 B2 * | 1/2005 | Loeb et al. | 385/33 |
| 6,953,457 B2 * | 10/2005 | Farr et al. | 606/15 |
| 6,953,458 B2 * | 10/2005 | Loeb | 606/15 |
| 6,966,906 B2 * | 11/2005 | Brown | 606/15 |
| 7,273,451 B2 * | 9/2007 | Sekine et al. | 600/104 |
| 2003/0135091 A1 * | 7/2003 | Nakazawa et al. | 600/113 |
| 2004/0081423 A1 * | 4/2004 | Galarza | 385/146 |

FOREIGN PATENT DOCUMENTS

| | | | |
|---|---|---|---|
| JP | 07-275254 | | 10/1995 |
| JP | 08-155033 | | 6/1996 |
| JP | 09-028665 | | 2/1997 |
| JP | 2003-210392 | | 7/2003 |
| JP | 2003001465 | * | 8/2003 |

OTHER PUBLICATIONS

Japanese Office Action for corresponding Japanese Application 2005-043598; dated Feb. 24, 2010.

* cited by examiner

*Fig. 1*  Inspecting inside of the small bowel with an ileus tube

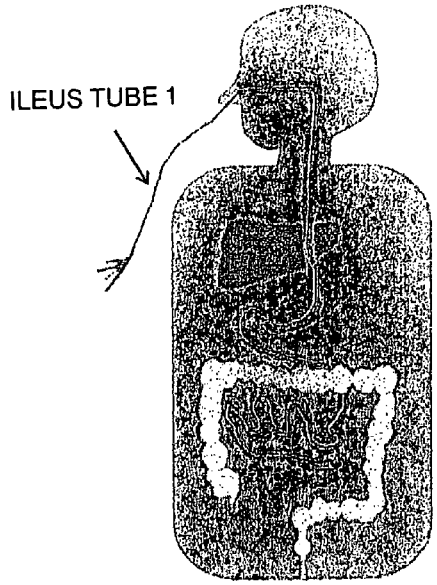

ILEUS TUBE 1

*Fig. 2*  Small bowel endoscope used with an ileus tube (in transverse section)

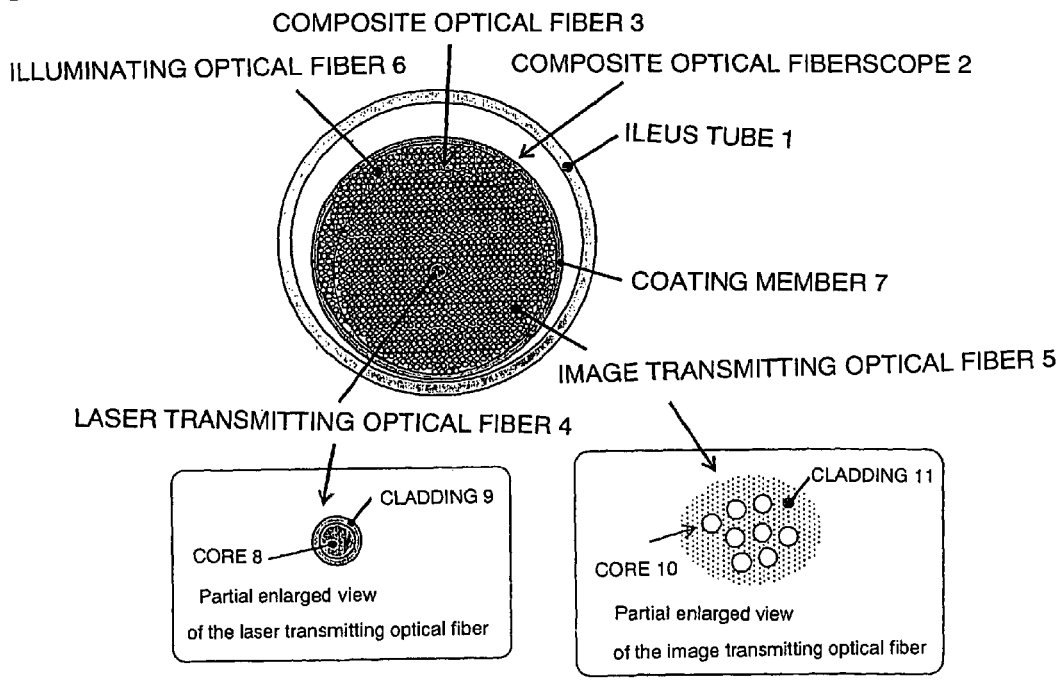

COMPOSITE OPTICAL FIBER 3
ILLUMINATING OPTICAL FIBER 6
COMPOSITE OPTICAL FIBERSCOPE 2
ILEUS TUBE 1
COATING MEMBER 7
IMAGE TRANSMITTING OPTICAL FIBER 5
LASER TRANSMITTING OPTICAL FIBER 4

CLADDING 9
CORE 8
Partial enlarged view of the laser transmitting optical fiber

CLADDING 11
CORE 10
Partial enlarged view of the image transmitting optical fiber Fig.3 Small bowel endoscope used with an ileus tube (in longitudinal section)
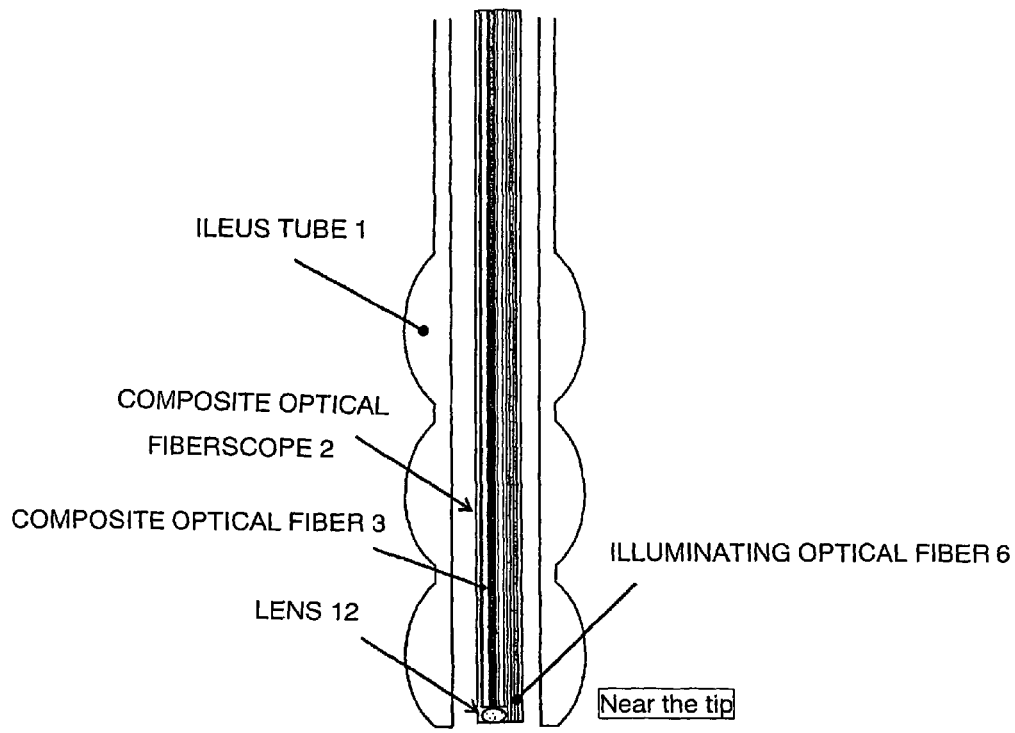
Fig.4 Shape of the coating member
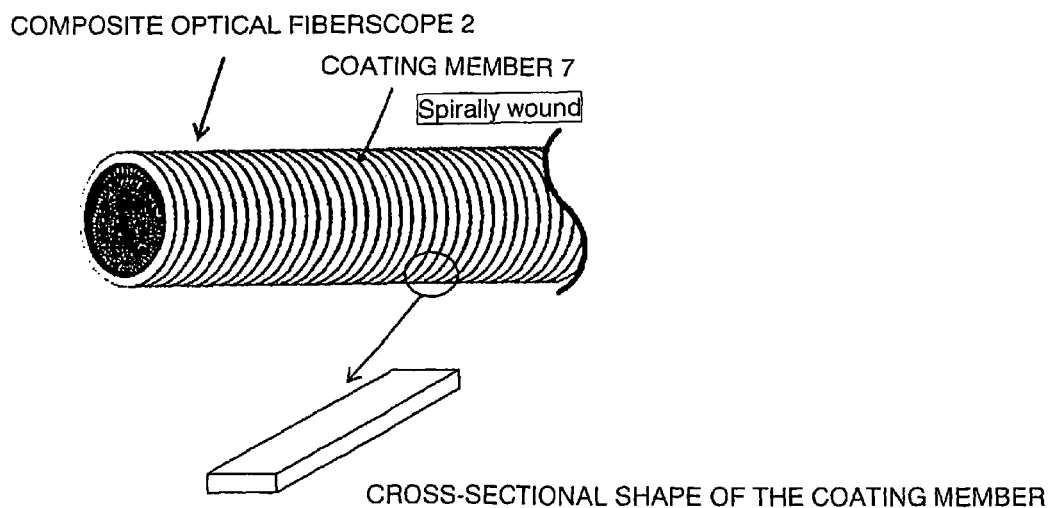

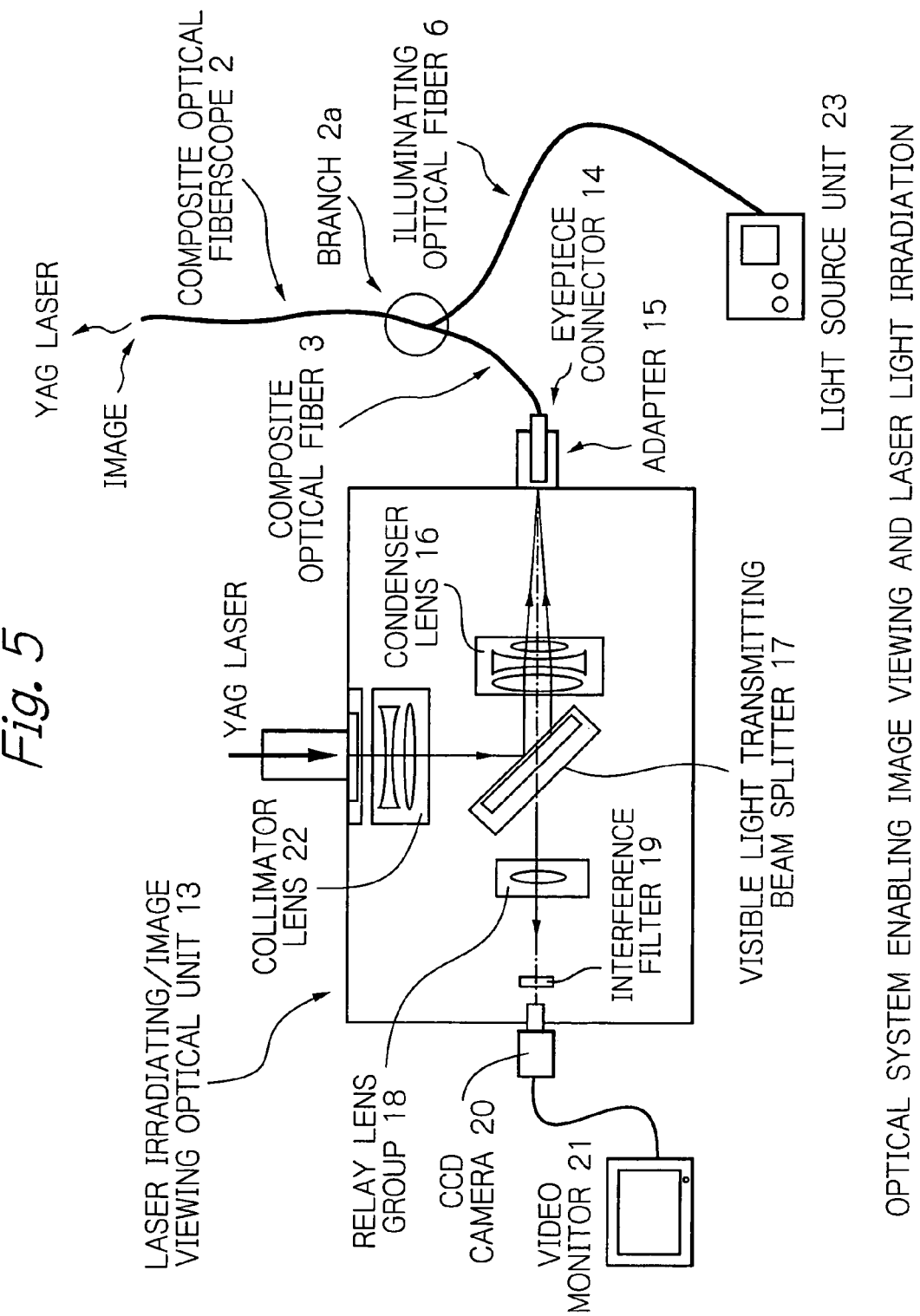

SMALL BOWEL ENDOSCOPE OF ILEUS TUBE TYPE THAT ENABLES LASER INSPECTION AND THERAPY

BACKGROUND OF THE INVENTION

This invention relates to an endoscopic system primarily intended for medical application to patients suffering from ileus and persons who have recovered from the disease. The endoscopic system comprises an ileus treating tube and a fine composite optical fiber as an integral assembly of an image transmitting image fiber for use in detecting and diagnosing a lesion and an optical fiber for transmitting laser light that is primarily used in inspecting and treating the lesion; the system is characterized in that it is used after the composite optical fiber is inserted into and made integral with the ileus treating tube.

Heretofore, endoscopes using optical fibers such as a fused monolithic image fiber or an image bundle have been commercialized in various types. Transmitting laser light to the lesion over the optical fiber is also a commercialized technique in laser therapy. Conventionally, the endoscope and the laser transmitting fiber are physically independent of each other and they must be inserted into the human body either through separate holes or via the lumens of catheter tubes.

For use in inspecting the interior of the small bowel, endoscopes of types other than the common type have also been commercialized and they include a push type, a ropeway type, a probe type, a double balloon type, and a capsule type. The problem is that these conventional endoscopes are only applicable in inspecting the small bowel of subjects who are not suffering from ileus or who have recovered from it.

Primarily for metal cutting and welding purposes, there have been proposed the following laser working methods and systems that employ a composite optical fiber:
(1) a laser working apparatus and a laser working method that uses the apparatus (JP 9-216086 A);
(2) a laser working apparatus and a laser working method that uses the apparatus (JP 9-216087 A);
(3) a laser working system using a composite optical fiber (JP 2003-1465 A); and
(4) an endoscopic system using an extremely fine composite optical fiber (JP 2004-47579 A).

Among these inventions, (4) relates to an endoscopic system primarily intended for medical applications and it is characterized by the use of an extremely fine composite optical fiber as an integral assembly of an image transmitting image fiber for use in detecting and diagnosing a lesion and an optical fiber for transmitting laser light that is primarily used in inspecting and treating the lesion.

However, no means exist that can solve the problems with the conventional small bowel inspecting procedures and ileus treating tubes by applying and improving the heretofore proposed techniques for the purpose of performing inspection and treatment within the small bowel.

In all conventional endoscopic systems for laser therapy, the endoscope which is responsible for image observation is physically independent of the laser light transmitting optical fiber, so in a separate step from checking the image of the lesion through the endoscope, the doctor inserts the laser light transmitting optical fiber into the human body until it comes close enough to the lesion and performs treatment by applying laser light to the lesion while checking the position of the optical fiber with the aid of the image obtained with the endoscope.

This procedure requires that the surgeon perform laser application by first checking the lesion and the optical fiber imagewise via the endoscope and then, on the basis of the obtained image information, exercising his or her discretion in directing the tip of the optical fiber to the desired position with respect to the lesion.

However, directing the tip of the laser transmitting optical fiber to the desired position with respect to the lesion largely depends on the skill and discretion of the surgeon and so does the accuracy with which the applied laser light can fall on the target position of the lesion.

The endoscope most commonly used to examine the inside of the small bowel is of a push type which is readily available (by rental) and easy to operate; however, the range that can be examined by this method is limited to the upper part of the small bowel and, what is more, the subject may suffer a pain. An endoscope of a ropeway type has a problem in that if the bowel tract has a constriction, the string may become entangled at the mouth of the constricted area to form a knot, which can be neither passed through nor extracted from the constriction. Similarly, an endoscope of a probe type does not function if the bowel tract has a constricted area. On the other hand, the recently developed endoscopes of a double balloon type and a capsule type have a potential to become standards in the art of image inspection of the small bowel. The capsular endoscope causes little pain to the subject but it has the problems of defying not only manipulation of the image taking process but also biopsy while involving the need to perform prior check for a constriction in the bowel tract. The double balloon type endoscope not only enables almost all part of the small bowel to be examined but it also allows treatments such as biopsy and polypectomy. The problems are the need to perform a pretreatment nearly as extensive as general anesthesia, increasing the complexity of the operation, and that the endoscope is difficult to insert into the bowel tract if it has a constriction. Thus, the conventional procedures of inspecting the interior of the small bowel have a common problem in that they cannot be used in diagnosing and treating patients suffering from ileus.

With a view to performing external radiography (examination with x-rays) on patients suffering from ileus, a contrast agent is administered to an area near the lesion through an ileus tube. The ileus tube is inserted into the subject's nostril and pushed farther to reach the site of interest with the position of its tip being checked by means of continued radiography. When the tip of the ileus tube has come near the duodenum in the process, air or water is externally supplied into the balloon attachment to inflate the tube, which is thereafter delivered deep into the bowel by means of its vermicular movement. In the meantime, gastrointestinal juice may be aspirated through a suction port provided near the tip of the ileus tube. After the tip of the ileus tube has reached the intended position in the small bowel, a contrast agent is injected from the outside and the lesion is examined by radiography. Two problems with the ileus tube are that it does not permit examination with the naked eye and that the surgeon is not capable of manipulating the tip of the tube at will.

SUMMARY OF THE INVENTION

The present invention has been accomplished under those circumstances and has as an object providing a small bowel endoscopic system of an ileus tube type using a monolithic composite optical fiber that can be applied with an ileus tube employed to administer a contrast agent or the like to a patient suffering from ileus and which is an integral assembly of a large-diameter optical fiber with a core/cladding structure intended for laser light transmission and a multi-core image fiber section surrounding that optical fiber to enable image transmission.

The present inventors have invented a means for solving the problems with the conventional small bowel inspecting procedures and ileus treating tubes by applying and improving the heretofore proposed techniques for the purpose of performing inspection and treatment within the small bowel.

BRIEF DESCRIPTION THE DRAWINGS

FIG. 1 depicts how the interior of the small bowel is inspected with an ileus tube;

FIG. 2 is a cross-sectional view of a small bowel endoscope used with an ileus tube;

FIG. 3 is a longitudinal section of the small bowel endoscope used with an ileus tube;

FIG. 4 depicts a coating member as applied to a composite optical fiberscope; and FIG. 5 shows a layout of optics that enables image viewing and laser light application.

DETAILED DESCRIPTION OF THE INVENTION

FIG. 1 shows schematically a use of an ileus tube. The ileus tube indicated by 1 is inserted into the subject's nostril and pushed farther to reach the site of interest with the position of its tip being checked by means of radiography (irradiation with x-rays). When the tip of the ileus tube has become near the duodenum in the process, air or water is externally supplied into the balloon attachment to inflate the tube, which is thereafter delivered deep into the bowel by means of its vermicular movement. After the tip of the ileus tube 1 has arrived at the intended position in the small bowel, a contrast agent is injected from the outside and the lesion is examined by radiography. In the meantime, gastrointestinal juice may be aspirated through a suction port provided near the tip of the ileus tube 1.

FIGS. 2 and 3 are schematic representations of a composite optical fiberscope 2 in a transverse and a longitudinal section, respectively, as it has been inserted into the ileus tube 1. Indicated by numeral 3 is a composite optical fiber inserted into the ileus tube 1 and it comprises a large-diameter laser transmitting optical fiber 4 in the center which is primarily intended for laser transmission and surrounded by a large number of image transmitting optical fibers 5 that are bundled together. The laser transmitting optical fiber 4 consists of a core 8 made of $GeO_2$ doped quartz glass and a cladding 9 made of pure quartz glass. The diameter of the core 8 is preferably in the range of 50-400 μm whereas the diameter of the cladding 9 preferably ranges from about 1.02 to about 1.3 times the core diameter. The numerical aperture (NA) of the laser transmitting optical fiber 4 (NA is an incident angle or acceptance angle through which light striking an end face of the optical fiber 4 can travel through the optical fiber 4) is typically set in an approximate range from 0.2 to 0.4.

The large number of image transmitting optical fibers 5 bundled together around the laser transmitting optical fiber 4 are fused to form a monolithic sea-island structure in which a large number of cores 10 as islands are surrounded by a continuous phase of cladding 11 like a sea. The cores 10 are made of $GeO_2$ doped quartz glass and the cladding 11 is made of either pure quartz glass or fluorine or otherwise doped quartz glass. Adjacent cores are spaced apart by a distance of about 3 μm. The number of the image transmitting optical fibers 5 in a bundle represents the number of pixels and it preferably ranges from about 1,000 to about 100,000. To make the composite optical fiber 3 in the embodiment under consideration, a rod of large-diameter laser transmitting optical fiber 4 is placed at the center of a quartz tube serving as a quartz jacket layer and then surrounded by optical fibers serving as image transmitting fibers 5 which are packed together to make a perform, which is then drawn down to form a smaller-diameter fiber.

An illuminating optical fiber 6 is preferably made of multi-component glass fibers. Other choices include quartz optical fibers and plastic clad optical fibers. All of these components are inserted into a coating member 7 and bonded to its inner surfaces to form the tip at the objective end of the fiberscope. The coating member may be a resin tube such as a fluoroplastic (PTFE or polytetrafluoroethylene, ETFE or tetrafluoroethylene/ethylene copolymer, or PFA or tetrafluoroethylene/perfluoroalkyl vinyl ether copolymer) tube, a polyurethane tube or a polyimide tube; alternatively, it may be a metal pipe such as a stainless steel pipe. A coating member that can be used in the embodiment under consideration is shown in FIG. 4; a shape-memory alloy composed of titanium and nickel and worked in a sheet approximately 0.003 mm thick and 0.005 mm wide is wound helically around itself into a tubular form. The coating member can recover the original shape upon external voltage or current control.

FIG. 5 shows a layout of optics that enables image viewing and laser light application to be done by the composite optical fiberscope 2 as it has been inserted into the ileus tube 1. The composite optical fiberscope 2 divides into the composite optical fiber 3 and the illuminating optical fiber 6 at a branch 2a. An eyepiece connector 14 is fitted to an adapter 15 on a laser irradiating/image viewing optical unit 13. The light traveling through the composite optical fiber passes through a condenser lens 16, a visible light transmitting beam splitter 17, a relay lens group 18 and an interference filter 19 for blocking the laser light, so that it is focused on a CCD camera 20. The image taken by the camera is displayed for viewing on a video monitor 21.

Speaking of the laser light, it is issued from a laser oscillator. The issued laser light passes through a collimator lens 22 in the laser irradiating/image viewing optical unit 13 and is reflected backward by the beam splitter 17; the reflected laser light then passes through the condenser lens 16 to be launched into the core 8 of the composite optical fiber 3.

Illuminating light for facilitating the viewing of image is transmitted over the illuminating optical fiber 6 connected to a light source unit 23.

After connecting the laser irradiating/image viewing optical unit to the composite optical fiberscope, laser oscillator, light source unit and the video monitor according to the layout shown in FIG. 5, the single fiberscope is inserted into the ileus tube which in turn is inserted into the small bowel of a patient with an ileus, whereby it becomes possible to effect image viewing within the patient's small bowel as it is irradiated with the laser light. This system ensures that the surgeon, while viewing the image of the lesion, can accurately apply the laser light to the lesion without having to depend on his or her skill and experience. In addition, viewing of the image of the ileus is performed not only during irradiation with laser light; it can be continued into the subsequent stage to the irradiation; therefore, the surgeon can avoid erroneous irradiation with laser light and, what is more, the subject can be irradiated with the required intensity of laser light over the required period of time by visually checking those conditions.

The laser light source can choose the most suitable light source depending on the severity of the lesion and the regimen of the treatment. For example, a variety of lasers having wavelengths ranging from the visible to the near infrared region may be employed and they include a dye laser, an argon ion laser, a semiconductor laser, a Nd:YAG laser, a Ho:YAG laser, etc. If the large-diameter core of the extremely fine composite optical fiber which serves as the laser light transmitting portion is made of pure quartz glass and the cladding is made of fluorine-doped quartz glass, an excimer laser such as XeCl, KrF or ArF may be used as the light source.

The following are typical examples of small bowel endoscopic laser therapy that may be practiced by using the endoscopic system of the present invention.

Laser Angioplasty

A bleeding site on the inner surface of the small bowel or the lesion of an inflammatory disease such as Crohn's disease or enteric tuberculosis is observed while at the same time, Nd:YAG laser light is directed at the target to coagulate it.

Diagnosis and Treatment Involving Application of Laser Light to Photosensitive Materials For treatment of a tumor in the small bowel, a material having tumor affinity and photosensitivity, say, a hematoporphyrin derivative (HpD) is administered. Tumor cells in which HpD has accumulated are irradiated with exciting laser light as from an excimer laser of extremely low energy, whereupon the HpD emits fluorescence. The resulting fluorescence spectrum peculiar to the HpD is detected in the image transmitting section and observed with a CCD camera as a two-dimensional image. Alternatively, the fluorescence spectrum may be connected to a spectroscope and analyzed for diagnostic purposes.

If desired, the laser light source may be switched over to a near infrared laser light source such as Nd:YAG laser and the lesion that has been found to be a tumor by diagnosis is irradiated with this laser light so that it is evaporated and cauterized for treatment. Similarly, cancer cells may be diagnosed and treated by laser light irradiation using photosensitive materials.

What is claimed is:

1. A small bowel endoscope which enables laser inspection and therapy in a small bowel, comprising:
    an ileus tube employed to administer a contrast agent or the like to a patient suffering from ileus, a tip of the ileus tube comprising sections arranged in series along its longitudinal direction, each of the sections having a ball-like shape to enable the tip of the ileus tube to reach an ileus area of the small bowel; and
    a composite optical fiber which is an integral assembly of
        a large-diameter optical fiber with a core/cladding structure intended for laser light transmission, and
        image transmitting optical fibers bundled together around the large-diameter optical fiber, being fused to form a monolithic sea-island structure in which a large number of cores as islands are surrounded by a continuous phase of cladding like a sea,
    wherein the composite optical fiber is inserted into and selectively slidable within the ileus tube.

2. A small bowel endoscope which enables laser inspection and therapy in a small bowel, comprising:
    an ileus tube employed to administer a contrast agent or the like to a patient suffering from ileus, a tip of the ileus tube comprising sections arranged in series along its longitudinal direction, each of the section having a ball-like shape to enable the tip of the ileus tube to reach an ileus area of the small bowel; and
    a composite optical fiber which is an integral assembly of
        a large-diameter optical fiber with a core/cladding structure intended for laser light transmission,
        image transmitting optical fibers bundled together around the large-diameter optical fiber, being fused to form a monolithic sea-island structure in which a large number of cores as islands are surrounded by a continuous phase of cladding like a sea
        and
        an illuminating optical fiber partly surrounding the multi-core image fiber,
    wherein the composite optical fiber is inserted into and selectively slidable within the ileus tube.

3. The small bowel endoscope according to claim 1, wherein the composite optical fiber is surrounded by a coating member.

4. A small bowel endoscope which enables laser inspection and therapy in a small bowel, comprising:
    an ileus tube a tip of the ileus tube comprising sections arranged in series along its longitudinal direction each of the sections having a ball-like shape to enable the tip of the ileus tube to reach an ileus area of the small bowel;
    a laser irradiating/image viewing optical unit;
    a composite optical fiberscope;
    a laser oscillator; and
    a light source unit and a video monitor, wherein
        a composite optical fiber and an illuminating optical fiber in the composite optical fiberscope are made to diverge at a branch, the composite optical fiber is fitted to the laser irradiating/image viewing optical unit via an eyepiece connector, and the light traveling through the composite optical fiber passes through a condenser lens, a visible light transmitting beam splitter, a relay lens group and an interference filter for blocking the laser light, so that it is focused on a CCD camera and while the image taken by the camera is displayed for viewing on the video monitor,
        the composite optical fiber includes image transmitting optical fibers bundled together around the large-diameter optical fiber, being fused to form a monolithic sea-island structure in which a large number of cores as islands are surrounded by a continuous phase of cladding like a sea, and the composite optical fiber being inserted into and selectively slidable within the ileus tube,
        the laser light being issued from the laser oscillator passes through a collimator lens in the laser irradiating/image viewing optical unit and is reflected backward by the beam splitter to pass through the condenser lens so that it is launched into the core of the composite optical fiber and travels through the core to irradiate an ileus in the small bowel of a patient, and
    illuminating light being transmitted over the illuminating optical fiber connected to the light source unit, whereby it becomes possible to effect image viewing within the patient's small bowel as it is irradiated with the laser light.

5. The small bowel endoscope according to claim 2, wherein the composite optical fiber is surrounded by a coating member.

6. A small bowel endoscope, comprising:
    an ileus tube, a tip of the ileus tube comprising sections arranged along its longitudinal direction, each of the sections having a ball-like shape to enable the tip of the ileus tube to reach an ileus area of the small bowel;
    a composite optical fiber configured to be inserted through the ileus tube in the small bowel enabling viewing iileus area within a patient's small bowel and applying laser therapy, the composite optical fiber including a large-diameter optical fiber with a core/cladding structure used to transmit laser light at a treatment site, image transmitting optical fibers bundled together around the large-diameter optical fiber, being fused to form a monolithic sea-island structure in which a large number of cores as islands are surrounded by a continuous phase of cladding like a sea, an illuminating optical fiber made of multi-component fibers partially surrounding the multi-core image fiber; and a coating member defining an outer limit of the composite optical fiber, wherein the composite optical fiber is inserted into and selectively slidable within the ileus tube.

7. The small bowel endoscope according to claim 1, wherein the ileus tube is provided with a balloon to enable the ileus tube to be delivered deep into the small bowel using a vermicular movement.

8. The small bowel endoscope according to claim 2, wherein the ileus tube is provided with a balloon to enable the ileus tube to be delivered deep into the small bowel using a vermicular movement.

9. The small bowel endoscope according to claim 4, wherein the ileus tube is provided with a balloon to enable the ileus tube to be delivered deep into the small bowel using a vermicular movement.

10. The small bowel endoscope according to claim 6, wherein the ileus tube is provided with a balloon to enable the ileus tube to be delivered deep into the small bowel using a vermicular movement.

11. The small bowel endoscope according to claim 1, wherein a suction port for aspirating gastrointestinal juice is provided near the tip of the ileus tube.

12. The small bowel endoscope according to claim 2, wherein a suction port for aspirating gastrointestinal juice is provided near the tip of the ileus tube.

13. The small bowel endoscope according to claim 4, wherein a suction port for aspirating gastrointestinal juice is provided near the tip of the ileus tube.

14. The small bowel endoscope according to claim 6, wherein a suction port for aspirating gastrointestinal juice is provided near the tip of the ileus tube.

\* \* \* \* \*

UNITED STATES PATENT AND TRADEMARK OFFICE
CERTIFICATE OF CORRECTION

PATENT NO.        : 8,945,195 B2
APPLICATION NO.   : 11/356123
DATED             : February 3, 2015
INVENTOR(S)       : Kiyoshi Oka et al.

Page 1 of 1

It is certified that error appears in the above-identified patent and that said Letters Patent is hereby corrected as shown below:

Claims

Claim 2, Column 6, Line 5

Delete "sea" and insert --sea,--, therefor.

Claim 6, Column 6, Line 65

Delete "iileus" and insert --ileus--, therefor.

Signed and Sealed this
Thirteenth Day of October, 2015

Michelle K. Lee
*Director of the United States Patent and Trademark Office*